United States Patent
Snow et al.

(12)

(10) Patent No.: US 6,596,097 B1
(45) Date of Patent: Jul. 22, 2003

(54) METHOD OF COATING A METAL SUBSTRATE WITH A RADIOACTIVE LAYER

(75) Inventors: Robert Snow, West Chester, PA (US); Gregory McIntire, West Chester, PA (US); Edward Bacon, Audubon, PA (US); Evan Gustow, Villanova, PA (US)

(73) Assignee: Amersham, PLC, Little Chalfont (GB)

( * ) Notice: Subject to any disclaimer, the term of this patent is extended or adjusted under 35 U.S.C. 154(b) by 0 days.

(21) Appl. No.: 09/577,441

(22) Filed: May 24, 2000

Related U.S. Application Data

(60) Provisional application No. 60/138,931, filed on Jun. 11, 1999.

(30) Foreign Application Priority Data

Jul. 5, 1999 (GB) ................................................ 9915714

(51) Int. Cl.$^7$ ............................................... C23C 18/16
(52) U.S. Cl. ...................... 148/283; 148/253; 148/243; 148/264
(58) Field of Search ................................. 148/283, 253, 148/243, 264

(56) References Cited

U.S. PATENT DOCUMENTS

| 4,323,055 A | 4/1982 | Kubiatowicz |
| 4,654,170 A | * 3/1987 | Murray ....................... 252/626 |

FOREIGN PATENT DOCUMENTS

| EP | 0 996 130 A1 | 4/2000 |
| WO | WO 00/09212 | 2/2000 |

* cited by examiner

*Primary Examiner*—Roy King
*Assistant Examiner*—Harry D. Wilkins, III

(57) ABSTRACT

A method for the immobilization of a radioactive anion on the surface of a metal substrate, said method comprising treating the substrate with an oxidizing agent in the presence of a solution of a radioactive anion which forms an insoluble salt with ions of said metal. Preferably, a binding agent will also be present. Preferably, the metal is silver, the radioactive anion is $^{125}I^-$ and the binding agent comprises bromide ions.

17 Claims, No Drawings

METHOD OF COATING A METAL SUBSTRATE WITH A RADIOACTIVE LAYER

This application claims the benefit of U.S. Provisional Application No. 60/138,931, filed Jun. 11, 1999.

BACKGROUND OF INVENTION

Brachytherapy is a general term covering medical treatment which involves placement of a radioactive source near a diseased tissue and may involve the temporary or permanent implantation or insertion of a radioactive source into the body of a patient. The radioactive source is thereby located in proximity to the area of the body which is being treated. This has the advantage that a high dose of radiation may be delivered to the treatment site with relatively low dosages of radiation to surrounding or intervening healthy tissue.

Brachytherapy has been proposed for use in the treatment of a variety of conditions, including arthritis and cancer, for example breast, brain, liver and ovarian cancer and especially prostate cancer in men (see for example J. C. Blasko et al., *The Urological Clinics of North America*, 23, 633–650 (1996), and H. Ragde et al., *Cancer*, 80, 442–453 (1997)). Prostate cancer is the most common form of malignancy in men in the USA, with more than 44,000 deaths in 1995 alone. Treatment may involve the temporary implantation of a radioactive source for a calculated period, followed by its removal. Alternatively, the radioactive source may be permanently implanted in the patient and left to decay to an inert state over a predictable time. The use of temporary or permanent implantation depends on the isotope selected and the duration and intensity of treatment required.

Permanent implants for prostate treatment comprise radioisotopes with relatively short half-lives and lower energies relative to temporary sources. Examples of permanently implantable sources include iodine-125 or palladium-103 as the radioisotope. The radioisotope is generally encapsulated in a titanium casing to form a "seed" which is then implanted. Temporary implants for the treatment of prostate cancer may involve iridium-192 as the radioisotope.

Recently, brachytherapy has also been proposed for the treatment of restenosis (for reviews see R. Waksman, *Vascular Radiotherapy Monitor*, 1998, 1, 10–18, and *MedPro Month*, January 1998, pages 26–32). Restenosis is a re-narrowing of the blood vessels after initial treatment of coronary artery disease.

Coronary artery disease is a condition resulting from the narrowing or blockage of the coronary arteries, known as stenosis, which can be due to many factors including the formation of atherosclerotic plaques within the arteries. Such blockages or narrowing may be treated by mechanical removal of the plaque or by insertion of stents to hold the artery open. One of the most common forms of treatment is percutaneous transluminal coronary angioplasty (PTCA)— also known as balloon angioplasty. At present, over half a million PTCA procedures are performed annually in the USA alone. In PTCA, a catheter having an inflatable balloon at its distal end is inserted into the coronary artery and positioned at the site of the blockage or narrowing. The balloon is then inflated which leads to flattening of the plaque against the artery wall and stretching of the artery wall, resulting in enlargement of the intraluminal passage way and hence increased blood flow.

PTCA has a high initial success rate but 30–50% of patients present themselves with stenotic recurrence of the disease, i.e. restenosis, within 6 months. One treatment for restenosis which has been proposed is the use of intraluminal radiation therapy. Various isotopes including iridium-192, strontium-90, yttrium-90, phosphorus-32, rhenium-186 and rhenium-188 have been proposed for use in treating restenosis.

Conventional radioactive sources for use in brachytherapy include so-called seeds, which are sealed containers, for example of titanium or stainless steel, containing a radioisotope within a sealed chamber but permitting radiation to exit through the container/chamber walls (U.S. Pat. Nos. 4,323,055 and 3,351,049). Such seeds are only suitable for use with radioisotopes which emit radiation which can penetrate the chamber/container walls. Therefore, such seeds are generally used with radioisotopes which emit γ-radiation or low-energy X-rays, rather than with β-emitting radioisotopes.

Brachytherapy seeds comprising a coating of radioactive silver iodide on a silver wire encapsulated inside a titanium container are known in the art (U.S. Pat. No. 4,323,055). Such seeds are formed by first chloriding or bromiding the silver to form a layer of silver chloride or bromide, and then replacing the chloride or bromide ions with radioactive iodide ions (I-125) by ion exchange. Such seeds are available commercially from Medi-Physics, Inc., under the Trade Name I-125 Seed® Model No. 6711 or OncoSeed™ Iodine-125 seeds (Nycomed Amersham).

Other conventional brachytherapy seeds comprise titanium containers encapsulating ion exchange resin beads onto which a radioactive ion, for example I-125, has been absorbed (U.S. Pat. No. 3,351,049). The immobilisation of a radioactive powder within a polymeric matrix has also been proposed (WO97/19706).

The processes disclosed in U.S. Pat. No. 4,323,055 for the production of I-125 containing seeds involve a number of separate steps. We believe a more efficient and rapid method for the production of radioactive sources comprising insoluble salts, especially silver salts, is desirable from a manufacturing viewpoint.

SUMMARY OF INVENTION

According to one aspect of the invention there is therefore provided a method for the immobilisation of one or more radioisotopes on the surface of a metal substrate, said method comprising treating the substrate with an oxidising agent to produce metal cations, in the presence of a source of a radioactive anion containing one or more radioisotopes, which anion forms an insoluble salt with said metal cations. Preferably, the radioactive anion will be present in solution or in a dispersion. Preferably, a binding agent will also be present. The products of the method of the invention are radioactive substrates.

Any metal which can form an insoluble salt with a radioactive anion on oxidation may be used as the metal substrate in the method of the invention. Suitable metals include silver, copper, lead, zinc, palladium, thallium, cadmium, lanthanum and gold. Preferably, the metal substrate is silver. The substrate may be made of solid metal or a suitable material plated with a layer of metal, for example silver, zinc, palladium or thallium. Suitable materials for plating include other metals, for example gold, copper or iron, and plastics, for example polypropylene, polystyrene, nylon, delrin, Kevlar™, and any other plastic or composite which can form a solid rod for plating with the metal of interest. Suitable plating methods are known in the art and include chemical deposition, sputtering and ion plating techniques.

The substrate should be of a suitable size and dimensions for incorporation into a source, for example a seed, for use in brachytherapy. Conventional seeds for use in the treatment of prostate cancer, for example, are typically substantially cylindrical in shape and approximately 4.5 mm long with a diameter of approximately 0.8 mm, such that they may be delivered to the treatment site using a hypodermic needle. For use in the treatment of restenosis, a source should be of suitable dimensions to be inserted inside a coronary artery, for example with a length of about 10 mm and a diameter of about 1 mm, preferably a length of about 5 mm and a diameter of about 0.8 mm, and most preferably with a length of about 3 mm and a diameter of about 0.6 mm. Sources for use in the treatment of restenosis are typically delivered to the treatment site using conventional catheter methodology.

Preferably, the substrate is of a suitable size and dimensions to fit inside a conventional seed container, such as those disclosed in U.S. Pat. No. 4,323,055 which is hereby incorporated by reference. Preferred seed containers are those made of titanium, titanium alloy or stainless steel. Preferably, the substrate will be substantially cylindrical in shape, for example in the form of a rod or wire. Suitable dimensions are about 3 mm long and about 0.10 mm to 0.70 mm in diameter, preferably about 0.5 mm in diameter.

Alternatively, the radioactive substrates may be incorporated into a polymer or ceramic matrix. Suitable polymer matrices include those disclosed in WO97/19706 which is hereby incorporated by reference. If the radioactive anion comprises a β-emitter, the radioactive substrate should not be encapsulated in a metal container as such containers would absorb the β-particles emitted and prevent them from reaching the treatment site.

If the metal substrate comprises silver or another X-ray opaque metal such as gold, copper or iron, there is the added advantage that sources comprising the radioactive substrate will be detectable by X-ray when inserted or implanted into a patient. Preferably, the substrate is shaped such that its orientation can also be determined by X-ray imaging. If the substrate comprises an X-ray transparent material plated with a metal such as silver, the radiopaque metal thickness is preferably greater than about 0.050 mm to ensure X-ray visualisation.

DETAILED DESCRIPTION OF INVENTION

The radioactive anions for use in the method of the invention may be simple anions such as $^{125}I^-$ or $^{35}S^{2-}$, or complex anions such as $^{32}PO_4^{3-}$, $^{35}SO_4^{2-}$ or $^{51}CrO_4^{2-}$. If the anion is a complex anion, it may comprise one or more radioisotopes, preferably one, two or three radioisotopes. More than one type of radioactive anion may be used together in the method of the invention, for example $^{125}I^-$ together with $^{35}SO_4^{2-}$. The choice of anion(s) and radioisotopes will depend in part on the intended use of the resulting brachytherapy source and the type of radiation which the sources should emit. For example, the radioactive anion may emit γ-radiation or low-energy X-rays, or it may be a β-emitter.

A radioactive anion which forms an insoluble salt with the metal of the metal surface of the substrate should be used. Preferred radioactive anions include those comprising $^{125}I^-$, $^{35}S$, $^{32}P$ or $^{33}P$. Possible anions include $^{125}I^-$, $^{131}I^-$, $^{123}I^-$, $^{35}S^{2-}$, $^{35}SO_4^{2-}$, $^{35}SO_3^{2-}$, $^{125}IO_3^-$, $^{131}I^-$, $^{123}IO_3^-$, $^{51}CrO_4^{2-}$, $^{32}PO_4^{3-}$, $H^{32}PO_4^{2-}$ and $H_2^{32}PO_4^-$. For the purposes of the invention, a salt is considered to be insoluble if its solubility product constant is lower than about $1\times10^{-5}$, preferably less than about $1\times10^{-2}$ and most preferably less than $1\times10^{-16}$. For a sparingly soluble salt $M_xA_y$ in contact with its saturated solution, the solubility product is given by $K_{sp}=[M^{y+}]^x[A^{x-}]^y$.

Concentrations are normally given in moles/liter at 298° K. For example, if the metal is silver, suitable anions include those shown in the Table 1 below. Values are taken from the Handbook of Chemistry and Physics, 74$^{th}$ Edition, 1993–4, Section 8, page 49.

TABLE 1

| Compound | Ksp | Possible Radioisotopes |
|---|---|---|
| Silver(I) iodide | $8.51 \times 10^{-17}$ | $^{125}I, ^{131}I, ^{123}I$ |
| Silver(I) chromate | $1.12 \times 10^{-12}$ | $^{51}Cr$ |
| Silver(I) iodate | $3.0 \times 10^{-8}$ | $^{125}I, ^{131}I, ^{123}I$ |
| Silver(I) phosphate | $1.4 \times 10^{-16}$ | $^{32}P$ |
| Silver(I) sulfate | $1.4 \times 10^{-5}$ | $^{35}S$ |
| Silver(I) sulfide | $6.3 \times 10^{-50}$ | $^{35}S$ |
| Silver(I) sulfite | $1.5 \times 10^{-14}$ | $^{35}S$ |

Other possible anions include complex anions derived from pyrophosphoric acid, such as $H_3P_2O_7^-$, wherein one or more of H, P or O comprise a radioisotope. Suitable anions derived from pyrophosphoric acid are disclosed in WO97/49335 which is hereby incorporated by reference. When the metal surface is silver, a preferred anion is $^{125}I$-iodide.

One advantage of the method of the invention is that it is a "one-step" chemical reaction. The prior art chemical processes comprise two or more steps, which lead to longer preparation times, greater variability of iodide distribution and greater costs. The method of the invention is also readily applicable to substrates of a variety of different geometric shapes, for example spheres or rods. The method can be applied to a single substrate or to a plurality of substrates wherein the number of substrates can range from 2 to about 100,000 or more, for example in a batchwise process. Treatment of a metal substrate with an oxidizing agent in the presence of a radioactive anion in a one-pot reaction leads to immobilization of the anion on the substrate in situ. Preferably, both the oxidizing agent and the radioactive anion are used as solutions in the same solvent, for example in aqueous solution. Alternatively, a solid oxidising agent may be added to a reaction mixture comprising the metal substrate and a solution or dispersion of a radioactive anion.

The source of the radioactive anion may be present in solution in a suitable solvent. Alternatively, it may be present in the form of a dispersion or precipitate in a suitable liquid phase. For example, if the radioactive anion is iodide, it may be present as a dispersion of silver iodide, or a dispersion of any insoluble metal iodide salt which displays greater solubility than that of the insoluble radioactive salt to be formed using the method. For example, if the substrate is silver and the radioactive anion is iodide, the iodide source may be a dispersion of an iodide salt of copper, lead, palladium or thallium. Table 2 below shows the solubility of some iodide salts. Copper, lead, palladium and thallium iodide are all more soluble than silver iodide, and so could be used as an iodide source in the immobilisation of iodide ions on a silver substrate using the method of the invention. Gold iodide is less soluble than silver iodide and hence would not be a suitable iodide source in such a method using a silver substrate.

TABLE 2

| Salt | Ksp | equilibrium solubility (M) |
|------|-----|---------------------------|
| AgI | $8.3 \times 10^{-17}$ | $9.11 \times 10^{-9}$ |
| CuI | $1.1 \times 10^{-12}$ | $1.05 \times 10^{-6}$ |
| PbI$_2$ | $7.1 \times 10^{-9}$ | $\sim 1.3 \times 10^{-3}$ |
| PdI$_2$ | $1.0 \times 10^{-23}$ | $\sim 1.4 \times 10^{-8}$ |
| TlI | $6.5 \times 10^{-8}$ | $3.0 \times 10^{-4}$ |
| AuI$_3$ | $1.0 \times 10^{-46}$ | $1.4 \times 10^{-12}$ |

On oxidation of a silver substrate, the iodide should transfer from the dispersion to the surface of the substrate.

Alternatively, the source of radioactive iodide ions may be present in the form of an organic iodide-containing compound, for example an alkyl iodide such as 2-iodoethanol, ethyl iodide, iodobutylacetate, iodobutyric acid, 3-iodopropanol, epiiodohydrin, glyceryl iodide, an activated iodomethylcarbonyl compound such as iodoacetamide or iodoacetic acid, an iodinated lachrymator such as iodinated acetone or 1-iodo-2-(trimethylsilyl)acetylene, or an iodosilicon compound such as iodotrimethyl silane, each of which may degrade over the course of the immobilisation reaction to generate iodide ions in the solution phase.

Radioactive iodide ions may also be present in the form of a complex with a suitable complexing agent, for example starch, amylose, amylopectin, or another complex carbohydrate, which will gradually release iodine, and thence iodide ions, in the presence of hydroxide ions, into the solution phase over the course of the immobilisation reaction. Complexes of other radioactive anions may also be used in the method of the invention.

Alternatively, the radioactive anion source may be a suitable ion exchange resin bead with radioactive anions adsorbed thereon. Any ion exchange resin which can act as a reservoir for the radioactive anions may be used (for example, Pb$-2e^- \rightarrow$Pb$^{2+}$, Resin-SO$_4^{2-} \rightarrow$Resin+SO$_4^{2-}$, Pb$^{2+} \rightarrow$SO$_4^{2-} \rightarrow$PbSO$_4$).

Suitable oxidizing agents are known in the art, including those disclosed in U.S. Pat. No. 4,323,055 which is herein incorporated by reference. They include sodium chlorite (NaClO$_2$), sodium chlorate (NaClO$_3$), sodium chromate (Na$_2$CrO$_4$), hydrogen peroxide (H$_2$O$_2$), potassium dichromate (K$_2$Cr$_2$O$_7$), potassium permanganate (KMnO$_4$), and potassium ferricyanide (K$_3$Fe(CN)$_6$). For the immobilisation of iodide ions on silver metal, a preferred oxidizing agent is potassium ferricyanide.

The oxidizing agent and the metal should be chosen such that the oxidizing agent can oxidize the metal surface of the substrate under the reaction conditions. The metal cations thus formed at the surface of the substrate should combine with the radioactive anions in solution to form a layer of an insoluble salt on the surface of the substrate, thus immobilizing the anions on the surface of the substrate. Immobilization of a radioactive anion on the metal surface of a substrate provides a radioactive metal substrate.

Whether or not a particular oxidising agent is suitable for use in the method of the invention with a particular metal and a particular radioactive anion can be predicted by reference to the standard electrode potentials of the relevant half-reactions. If the sum of the standard electrode potentials for the oxidation half-reaction and the reduction half-reaction is positive, then in the absence of inhibiting kinetic effects, reaction should occur spontaneously. Tables of standard electrode potentials are readily available, for example in D. A. Skoog and D. M. West, Principles of Instrumental Analysis, Holt, Rinehart, and Winston, Inc., New York, 1971, pp 678–680, and W. M. Latimer, The Oxidation States of the Elements and Their Potentials in Aqueous Solution, Prentice Hall, Englewood Cliffs, N.J., 1952. A selection of standard electrode potentials (E$^\theta$) is shown in Table 2 below. Values are taken from Skoog and West.

TABLE 3

| Half reaction | E$^\theta$/volts | Possible radioisotopes |
|---------------|------------------|------------------------|
| AgI + e$^- \rightarrow$ Ag + I$^-$ | −0.152 | $^{125}$I, $^{123}$I, $^{131}$I |
| ½Ag$_2$S + e$^- \rightarrow$ Ag + ½S$^{2-}$ | −0.710 | $^{35}$S |
| $\alpha$Ag$_3$PO$_4$ + e$^- \rightarrow$ Ag + $\alpha$PO$_4^{3-}$ | +0.4878 | $^{32}$P, $^{33}$P |
| CuI + e$^- \rightarrow$ Cu + I$^-$ | −0.185 | $^{125}$I, $^{123}$I, $^{131}$I |
| PbSO$_4$ + 2e$^- \rightarrow$ Pb + SO$_4^{2-}$ | −0.356 | $^{35}$S |
| PbI$_2$ + 2e$^- \rightarrow$ Pb + 2I$^-$ | −0.365 | $^{125}$I, $^{123}$I, $^{131}$I |
| PbHPO$_4$ + 2e$^- \rightarrow$ Pb + HPO$_4^{2-}$ | −0.456 | $^{32}$P, $^{33}$P |
| MnO$_4^-$ + 8H$^+$ + 5e$^- \rightarrow$ Mn$^{2+}$ + 4H$_2$O | +1.51 | |
| Fe(CN)$_6^{3-}$ + e$^- \rightarrow$ Fe(CN)$_6^{4+}$ | +0.36 | |
| ½I$_2$ + e$^- \rightarrow$ I$^-$ | +0.54 | |

If the radioactive anion to be immobilised is iodide, then preferably an oxidising agent is chosen which will not oxidise iodide ions to molecular iodine under the reaction conditions. Molecular iodine is volatile and generation of a volatile radionuclide such as $^{125}$I$_2$ involves increased risk of exposure to radiation for the manufacturing personnel or, at least, rapid saturation of the carbon filters. However, if an oxidising agent is used which is strong enough to oxidise silver and to oxidise iodide to molecular iodine, the oxidation of the silver should occur preferentially as this is the more favourable reaction.

In one embodiment of the invention, ferricyanide is used as the oxidising agent. Under standard conditions, it is postulated that the reaction between ferricyanide and silver/silver iodide is very energetically favourable, i.e., $$E_{cell} = E_{cathode} - E_{anode}$$

$$E_{cell} = 0.36 - (-0.152)$$

$$E_{cell} = 0.512$$

while the possible reaction between ferricyanide and iodide would not be a spontaneous reaction under standard conditions, i.e., $$E_{cell} = 0.36 - (0.54)$$

$$E_{cell} = -0.18$$

Standard conditions are given as reagent activities of 1. For example, the concentration of both ferricyanide and the reduced form, ferrocyanide, would be equal to 1 molar.

However, the impact of concentration is predicted by the Nernst equation:

$$E\tfrac{1}{2}' = E\tfrac{1}{2}° - (0.059/n)\log(\text{reduced form/oxidised form}) \quad (i)$$

For the oxidising half cell, this becomes:

$$E\tfrac{1}{2}' = E\tfrac{1}{2}° - (0.059)\log([Ag°]/[Ag^+]) \quad (ii)$$

while the reduction half cell becomes:

$$E\tfrac{1}{2}' = E\tfrac{1}{2}° - (0.059)\log([Fe(CN)_6^{4-}]/[Fe(CN)_6^{3-}]) \quad (iii)$$

However, in the presence of iodide, the silver oxidation is coupled to the follow-up reaction as shown here:

$$\text{Oxidation: Ag}° \rightarrow \text{Ag}^+ + e^- \quad ^{125}\text{I}^- + ^{\text{Ag}+} \rightarrow \text{Ag}^{125}\text{I} \quad (iv)$$

The thermodynamics of equation (iv) are governed by the equilibrium constant, which for insoluble species is also known as the solubility product or $K_{sp}$ as shown here:

$$K_{sp}=[Ag^+][^{125}I^-] \quad (v)$$

Substituting equation (v) into equation (ii), the operative Nernst equation for the net reaction can be written as:

$$E\tfrac{1}{2}'=E\tfrac{1}{2}°-(0.059)\log([Ag^+]/(K_{sp}/[^{125}I^-]))$$

By rearranging the log term and grouping all the constants including the $K_{sp}$ term into a new $E\tfrac{1}{2}°'$, the impact of $[^{125}I^-]$ on the overall reaction can be seen:

$$E\tfrac{1}{2}'=\{E\tfrac{1}{2}°+(0.059)\log(K_{sp})\}-0.059\log[^{125}I^-] \quad (vi)$$

where $\{E\tfrac{1}{2}°+(0.059)\log(K_{sp})\}=E\tfrac{1}{2}°'$ for reaction (iv) above Accordingly, it is postulated that in the oxidation of silver by ferricyanide, the initial conditions and those throughout the process are as follows:

| Condition | Molar Ratio of $[Fe(CN)_6^{4-}]/[Fe(CN)_6^{3-}]$ | $[^{125}I^-]$ | $E_{cathode}$ | $E_{anode}$ | $E_{cell}$ |
|---|---|---|---|---|---|
| Initial | 1/1000 | 0.94 | 0.540 | −0.15 | 0.690 |
| 10% | 1/100 | 0.85 | 0.480 | −0.147 | 0.627 |
| 50% | 1 | 0.45 | 0.360 | −0.131 | 0.491 |
| 90% | 100/1 | 0.09 | 0.240 | −0.089 | 0.329 |
| 100% | 1000/1 | 0.01 | 0.180 | −0.033 | 0.213 |

This suggests that this reaction remains energetically favourable throughout the deposition of silver iodide.

The same type of process can be carried out for the possible side reaction of the oxidation of iodide to iodine. The operative Nernst equation for this half-cell is given by:

$$E\tfrac{1}{2}°=E\tfrac{1}{2}-(0.059/2)\log([I^-]^2/[I_2])$$

| Condition | Molar Ratio of $[Fe(CN)_6^{4-}]/[Fe(CN)_6^{3-}]$ | Ratio of $[I^-]^2/[I_2]$ | $E_{cathode}$ | $E_{anode}$ | $E_{cell}$ |
|---|---|---|---|---|---|
| Initial | 1/1000 | 1000/1 | 0.540 | 0.447 | 0.093 |
| 10% | 1/100 | 100/1 | 0.480 | 0.476 | 0.004 |
| 50% | 1 | 1 | 0.360 | 0.535 | −0.175 |
| 90% | 100/1 | 1/100 | 0.240 | 0.594 | −0.354 |
| 100% | 1000/1 | 1/1000 | 0.180 | 0.623 | −0.443 |

These calculations suggest that in the earliest part of the reaction, there is the chance to produce $^{125}I_2$ via oxidation by ferricyanide.

In a preferred embodiment of the invention, both ferricyanide and ferrocyanide are added to start the reaction to minimize the production of $^{125}I_2$. Preferably, ferricyanide and ferrocyanide are added at an initial molar ratio of $10=[Fe(CN)_6^{3-}]/[Fe(CN)_6^{4-}]$. In particular, an aqueous solution prepared from potassium ferricyanide and potassium ferrocyanide trihydrate can be made and added to the reaction vial. It is postulated that the presence of the ferrocyanide reduces the propensity for the side reaction to occur while the energetics behind the oxidation of silver to silver iodide remain very good. Those skilled in the art will recognize that similar reactions can occur in the presence of other redox couples.

The more resistant the metal is to oxidation, the stronger the oxidising agent should be. For example if the metal substrate is gold, a more powerful oxidizing agent such as permanganate may be used in the method of the invention.

The amount of oxidising agent required may be readily calculated by a skilled person depending on the amount of radioactive anion it is desired to immobilize on the metal substrate.

The amount of the radioactive anion, for example the concentration of a solution of the radioactive anion, can be chosen depending on the activity level desired in the resultant brachytherapy source. For example, substantially all of the anions present may be radioactive (i.e. "hot") or the radioactive anions may be diluted with non-radioactive (i.e. "cold" or carrier) anions. For example, radioactive $^{125}I$-iodide may be diluted with non-radioactive $^{127}I$-iodide. Conventional brachytherapy sources for use in the treatment of prostate cancer normally have activities in the region of 0.2 to 1.5 mCi. Using the method of the invention, coated substrates with an activity of up to as high as about a Curie may be prepared. Such substrates, and radioactive sources comprising such substrates, form further features of the invention.

In order for the insoluble salt to form a stable layer which is strongly bound to the metal substrate and which does not flake or fail to adhere to the substrate, it may be necessary to also use a binding agent in the method of the invention. The binding agent preferably comprises a non-radioactive anion which also forms an insoluble salt with cations of the metal and which is different to the radioactive anion. Preferably, the salt formed by cations of the metal with the binding agent will be less insoluble, i.e. more soluble than that formed by the radioactive anion with cations of the metal or with the binding agent counter-ion. For example, if the radioactive anion is $^{125}I$-iodide, suitable binding agents include chloride or bromide ions, preferably bromide ions.

Whether or not a binding agent is required in any particular case will depend, at, least in part, on the nature of the metal of the substrate and the radioactive anion to be immobilized. Whether or not a binding agent improves the stability of the coated substrate in a particular case may be determined by routine trial and error experiments.

The applicants do not wish to be bound by any particular theory regarding the rôle played by the binding agent in the method of the invention, but it is postulated that the binding anion is preferably physically smaller than the radioactive anion such that it can fit into gaps or cracks in the coating layer to help hold the layer together. It is also possible that the binding ions take part in establishing a template on the metal surface that affords a more adhesive layer of the insoluble salt of interest.

A layer comprising both the binding agent and the radioactive anion will form on the metal surface of the substrate. Provided the reaction is carried out with sufficient mixing e.g. stirring or agitation, the radioactive anion can be homogeneously distributed throughout this layer. Silver substrates coated using the prior art two-step process of U.S. Pat. No. 4,323,055 comprise the radioactive anion in a layer of silver iodide on the surface of a silver bromide-coated silver substrate.

If the metal is silver and the radioactive ion is $^{125}I$-iodide, carrying out the method of the invention in the presence of an excess of bromide ions leads to formation of a more physically stable layer than if the bromide ions are not present. The binding agent thus enhances adherence of the $Ag^{125}I$ salt to the surface of the substrate. In addition, the use of bromide ions as a binding agent leads to formation of AgBr on the surface of the substrate in addition to $Ag^{125}I$. The AgBr may form a coating over some or all of the $Ag^{125}I$, which may help to minimize loss of radioactivity from the source due to physical handling of the coated substrate. It is postulated that the small amount of bromide ion present may serve to help establish the crystal form of the resulting AgI such that it is a more cohesive layer, and adhesive to the metal substrate. In one embodiment, the molar ratio of bromide to iodide present in the surface layer of the substrate is preferably in the range of 2.25 to 2.75 and, more preferably 2.5.

In one embodiment of the invention, I-125 may be immobilised on a silver substrate by treating the substrate with a solution or dispersion comprising I-125 ions and bromide ions and a solution of an oxidising agent, for example an aqueous solution of potassium ferricyanide. The I-125 and bromide ions may, for example, be present as an aqueous solution of $Na^{125}I$ and NaBr. Alternatively, the source of I-125 ions may be a dispersion of $Ag^{125}I$ in a suitable solution phase, for example an aqueous solution.

It is postulated that in this embodiment the following reactions occur:

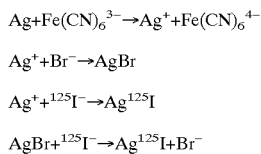

If the I-125 ions are present as a dispersion of $Ag^{125}I$, some of the $Ag^{125}I$ will gradually dissolve as the immobilisation reaction progresses thus generating I-125 iodide ions in solution. I-125 ions in solution may react directly with the oxidised silver (i.e. the $Ag^+$ cation) to form $Ag^{125}I$. Alternatively, the oxidised silver may react first with bromide ions to form AgBr, followed by ion-exchange of I-125 iodide for bromide to give $Ag^{125}I$. Thus both oxidation of the silver and formation of AgBr will result in removal of I-125 from the solution phase. Substantially all of the I-125 from the solution phase is therefore immobilised on the substrate using the method of the invention. The radioactivity of the product is therefore highly dependent on the effective concentration of $^{125}I$ or on the amount of $^{125}I$ effectively available in the initial solution phase.

When a plurality of substrates, for example metal wires or metal coated substrates such as metal coated organic compositions including metal coated plastics or polymers, or metal coated inorganic compositions such as metal coated ceramics or glasses are treated together, the nominal amount of radioactive ion that is immobilized on the metal surface of each substrate can vary from substrate to substrate giving rise to a statistically normal distribution of an average amount of radioactivity per substrate. In a kinetically rapid reaction, the width of the statistical distribution may be controlled to some extent by increasing the volume of the reacting solution without increasing the amount of reagents, thereby effectively diluting the reagents and slowing the reaction. In addition, applicants have unexpectedly observed that the presence of a salt additive to the reaction mixture at elevated concentrations can narrow the statistical distribution of the amount of radioactivity per substrate. One possible explanation is that the increased concentration of ions in the solution decreases the solution activity coefficient of the ions of interest (i.e. the radioactive anions and/or the binding agent) and hence slows the reaction.

The concentration of salt additive can range from about 0.01 molar up to saturation levels of the salt in solution, the latter varying as a function of the salt and temperature of the solution. For example, useful salts include NaCl which has a saturation level of about 357 grams per liter in water at 0° C. and about 391.2 grams per liter in water at 100° C.; KCl which has a saturation level of about 347 grams per liter in water at 30° C. and about 567 grams per liter in water at 100° C.; CsCl which has a saturation level of about 745 grams per liter in water at 20° C. and about 1590 grams per liter in water at 100° C.; LiCl which has a saturation level of about 637 grams per liter in water at 0° C. and about 1300 grams per liter in water at 95° C.; and $MgCl_2$ which has a saturation level of about 542.5 grams per liter in water at 20° C. and about 727 grams per liter in water at 100° C.; and $NaNO_3$ which has a saturation level of about 921 grams per liter in water at 20° C. and about 1800 grams per liter in water at 100° C. A number of these chloride and nitrate salts have been evaluated and shown to be effective at narrowing the statistical distribution of the amount of radioactive anion, for example iodide, present from substrate to substrate.

The saturation levels of other useful highly soluble salts can be found in the Handbook of Chemistry and Physics, CRC Press, 55th Edition. Saturated solutions of added salts can be achieved when an excess of undissolved salt is present in the reaction mixture in equilibrium with dissolved salt. The optimum level of ionic strength per added salt or mixtures of added salts which promotes the narrowest distribution of radioactivity uptake per substrate can be readily found by one skilled in the art using routine experimentation. At the end of the immobilisation reaction leading to uptake of radioisotope onto the metal substrate to form a radioactive substrate, excess salts can be removed by washing the substrate with aliquots of water.

Without the added volume or the added salt, the statistical distribution of radioactivity on the individual substrates is critically dependant upon the rate of mixing. Distributions ranging from 5 to 15% (relative standard deviation) are often observed. With the addition of increased volumes, these values drop to <6% (relative standard deviation). Addition of 2 M NaCl unexpectedly results in distributions <3% (relative standard deviation). The additional chloride ions may not take part in the reaction, but may simply decrease the activity coefficient of the reacting ions (e.g., bromide and iodide) thereby decreasing the critical dependence on the rates of mixing of the reagents themselves. It is, however, known that silver chloride is appreciably soluble in concentrated alkali chlorides where chloro complexes are formed (see Cotton, F. A. and Wilkinson, G. in Advanced Inorganic Chemistry, Interscience Publishers, John Wiley and Sons, page 863, 1962).

If the radioactive anion is present as a dispersion or in the form of a complex or a degradable compound, there may be the advantage that thorough mixing of the substrate(s), the oxidizing agent and the source of the radioactive anion occurs before the immobilisation reaction begins, leading to a more even distribution of the radioactive anions over the substrate(s)

The use of organic salts of the radioactive anions might also be useful at slowing the reaction of iodide with the silver wires, for example pyridinium iodides may be useful as an iodide source using this approach. Adding the radioactive anion to the reaction mixture as a solid salt may also be useful as the kinetics of dissolution may slow down the exposure of the wires to solution phase anion until mixing is completed. While the solid salt is not insoluble, the change from the solid phase to the solution phase could accomplish the desired alterations in the speed of the reaction.

In the specific case of the immobilisation of radioactive iodide ions on a plurality of silver substrates using potassium ferricyanide as the oxidising agent and bromide ions as a binding agent, the addition of >1 M NaCl to the reaction mixture gives rise to a yellow green precipitate shortly after the addition of the potassium ferricyanide. This green precipitate clears as the substrates coat with a mixed silver bromide/silver iodide salt. Chemical analysis of the precipitate shows high levels of silver and trace levels of iron suggesting the nature of the precipitate to comprise silver halide. This precipitation may allow mixing to occur before the bulk of the oxidation takes place, thereby ensuring a better distribution of iodide amongst the individual substrates.

Some metal halides, for example silver halides, are light-sensitive. Among the silver halides, silver bromide is most light-sensitive, followed by silver chloride and silver iodide respectively. One disadvantage of the prior art process of U.S. Pat. No. 4,323,055 for forming silver iodide-coated silver wires was that the light-sensitivity of the silver iodide meant that the process could not be carried out under natural light, but had to be carried out under red light.

A further significant advantage of the method of the present invention is that it need not be carried out under safe lights but can be carried out under normal room (fluorescent) lights. While a colour change is observed during the washing and drying steps from lime green of the initial coated wires to a darker, olive green for dried coated wires, analyses for iodide content either by radiochemical analysis or by the spectrophotometric method described in Example 1 below do not reveal any change in amount or loss of iodide from the coated wires. Better than 99% uptake is consistently achieved under normal, fluorescent lighting. It is possible that since the iodide is distributed throughout the deposited layer using the method of the invention, the light sensitivity is not critical, whereas the previous process resulted in Iodide deposited onto the surface of an existing AgBr coating, thereby exposing the AgI directly to any light incident upon the wires. This significantly improves the ease of manufacture and handling and avoids the need for expensive dark room facilities. It also significantly improves working conditions for those personnel involved in the manufacturing process and improves the morale of the manufacturing team.

EXAMPLES

The method of the invention will be further illustrated with reference to the following non-limiting Examples.

In the Examples, those skilled in the art will recognize that cold (i.e. non-radioactive) iodide can easily be replaced with radioactive iodide to render any Example germane for radioactive uses. For example, radioactive iodide solutions are specified with respect to levels of activity known as the specific activity. Generally, these activities are as high as 17 Curies/mg of iodide and may drop to very low levels. Thus, if an Example deposits 10 µg of cold iodide per wire, it is an easy calculation to confirm that those wires would contain 170 mCi each if the reaction was carried out using radioactive iodide with a specific activity of 17 Curies/mg iodide.

In all the Examples, the silver wires used were 2.8 mm long by 0.5 mm in diameter. Reaction vials were precoated with a silicone polymer.

Example 1

One Step Preparation of Silver Iodide/Silver Bromide Coated Silver Wires

500 Silver wires, having been cleaned by rinsing with heptane followed by acetone and dried, were loaded into a squared (four-sided) glass vial (15 ml) together with 51.5 mg of NaBr (as 0.515 ml of a 100 mg/ml NaBr aqueous stock solution) and 0.126 µl of a 0.1M NaI/0.01 M NaOH solution. The final volume was then adjusted to 3.5 ml with water for injection. The vial was then placed into a rotator at a fixed angle of 30 degrees from horizontal. The rotator was then turned on at 30 rpm and 1 ml of a 41.2 mg/ml aqueous solution of potassium ferricyanide ($K_3Fe(CN)_6$) was added to the contents of the vial to initiate the reaction. The resulting pale green solution was rotated for an hour to complete the reaction.

Twenty of the resulting wires were individually extracted with concentrated ammonium hydroxide overnight to dissolve the silver halide coating for analysis by ultraviolet spectrophotometry. While other analytical methods can be envisioned, this approach afforded rapid, easy analysis with sufficient sensitivity for assay of each wire. The results show that the wires were coated with a mixture of silver bromide and silver iodide with approximate concentrations of 18 µg of $Br^-$ and 3.2 µg of $I^-$ on each wire. This is more than sufficient to make wires with activities as high as 100 mCi each for use in brachytherapy devices, when sufficient amounts of $^{125}I$ are used in the reaction.

Example 2

Repetitive Preparation of Silver Iodide/Silver Bromide Coated Silver Wires

Five batches of 500 wires were prepared as described in Example 1. The data for each batch are shown below and demonstrate excellent reproducibility as well as a narrow standard deviation for each batch.

| Batch | Average [I−]/wire (µg) | Relative standard deviation (%) |
|---|---|---|
| 1. | 4.76 | 3.1 |
| 2. | 4.60 | 4.1 |
| 3. | 4.72 | 5.0 |
| 4. | 4.77 | 5.0 |
| 5. | 4.82 | 4.8 |
| Overall | 4.74 | 4.7 |

Example 3

One Step Preparation of Silver Iodide/Silver Bromide Coated Silver Wires Labelled with $Ag^{125}I$ 500 Wires were prepared as described in Example 1 except that an additional 8 micro Curies of $Na^{125}I$ were added to the non-radioactive NaI used in the reaction. Upon completion of the reaction, the variation in counts between wires (measured as dpm=disintegrations per minute) was found to be comparable to the data shown in Example 2. In addition, less than 1% of the total activity remained in the supernatant liquid suggesting >99% uptake of iodide ions by the wires in this one step preparation and no volatilization of the iodide into the atmosphere.

Example 4

One Step Preparation of Silver Iodide Coated Silver Wires

500 Wires were prepared as described in Example 1 except that no NaBr was added to the mixture. While the reaction took place to form a coating on the silver wires, that coating was not cohesively stable and began to flake off during the remainder of the coating process (i.e., the rest of the hour). This indicates that a binding agent may be necessary to form a cohesively stable layer containing AgI on a silver substrate.

Example 5

One Step Preparation of Silver Iodide Coated Silver Wires with Increased Amounts of Iodide on the Wire 500 Wires were prepared as described in Example 1 except that the amount of NaI used was increased to 30 µg/wire (approx 1.18 ml of 0.1 M NaI/0.001M NaOH). The reaction was successful in depositing both AgBr and AgI onto the wires. Each wire had an average amount of 30 µg I/wire.

Example 6

Kinetics of the Uptake of $^{125}$I from the Solution Phase in the Single Step Preparation of Silver Iodide/Silver Bromide Coated Silver Wires 500 Wires were prepared as described in Example 3 using an additional 8 micro Curies of Na$^{125}$I. Samples were taken from the supernatant liquid at various times to follow the loss of $^{125}$I from the solution phase. These data are expected to mirror the deposition of $^{125}$I onto the wire.

| Time (min.) | Counts (dpm) |
|---|---|
| 1 min | 122,242 |
| 2 min | 27,643 |
| 4 min | 6,111 |
| 8 min | 3,179 |
| 16 min | 3,381 |
| 32 min | 4,749 |
| 64 min | 4,595 |

(dpm = disintegration per minute)

These data indicate that >90% of the AgI layer was formed after the first 2 minutes. The slight increase in counts after 16 min probably resulted from prolonged rotation and tumbling which can cause physical removal of AgI from the wires.

Example 7

One Step Preparation of Silver Iodide Coated Silver Wires: 1500 Wire Batch Size

1500 Wires were prepared as described in Example 1 except that the amounts of NaI, NaBr, and K$_3$Fe(CN)$_6$, and the total reaction volume were increased three fold to account for the increased number of wires. In addition, a squared (four-sided) 25 ml vial was used to rotate the wires to accommodate the higher reaction volume (i.e. 13.5 ml). These conditions resulted in wires with an average, amount of iodide per wire of 4.693 µg/wire and a standard deviation of 0.427 (9.1%, relative standard deviation). These values compare well with earlier, smaller batches (see Example 2) and afford advantages of scale.

Example 8

Kinetics of the One Step Preparation of Silver Iodide Coated Silver Wires: 1500 Wire Batch Size 1500 Wires were prepared as described in Example 1 except that the amounts of NaI, NaBr and K$_3$Fe(CN)$_6$, and the total reaction volume were increased three fold to account for the increased number of wires. In addition, a squared (four-sided) 25 ml vial was used to rotate the wires to accommodate the higher reaction volume. A small amount of radioactive Na$^{125}$I was also added to afford quantitative assessment of the kinetics. 100 Microliter aliquots of the supernatant liquid were removed and counted at various time points to ascertain the kinetics of AgI formation on the silver wire.

| Time (min.) | Counts (dpm/100 µl) |
|---|---|
| 2 min | 13,431 |
| 4 min | 5,229 |
| 5 min | 5,186 |
| 16 min | 5,163 |

(dpm = disintegration per minute)

Again, these data indicate that >90% of the iodide uptake is over in 2 minutes.

Example 9

One Step Preparation of Silver Iodide Coated Silver Wires: 1500 Wire Batch Size and the Impact of Increased Volume 1500 Wires were prepared as described in Example 1 except that the amounts of NaI, NaBr and K$_3$Fe(CN)$_6$ were increased three fold to account for the increased number of wires. In addition, a squared (four-sided) 25 ml vial was used to rotate and tumble wires in the higher reaction volume. Experiments were carried out at total reaction volumes of 6.75 ml and 24 ml. The data below suggest that increased volumes can result in narrower distributions of iodide from wire to wire.

Volume=6.75 ml 24.0 ml

% relative 11.4 5.0 standard 12.9 3.8 deviation 15.4

Example 10

One Step Preparation of Silver Iodide Coated Silver Wires: 1500 Wire Batch Size and the Impact of Elevated Concentrations of an Added Salt: NaCl 1500 Wires were prepared as described in Example 1 except that the amount of NaI, NaBr, and K$_3$Fe(CN)$_6$ were increased three fold to account for the increased number of wires. In addition, a square 215 ml vial was used to rotate the wires due to the added reaction volume. Finally, the solution was made 2 M in NaCl. The results of replicate preparations at 1500 wires and then a repeat of a 500 wire batch as per Example 1 suggest that this level of NaCl has a beneficial effect on the standard deviation.

| | Relative Standard Deviation | |
|---|---|---|
| Volume (ml) Number of Wires/batch = | With NaCl 1500 500 | Without NaCl 1500 |
| 4.5 | | 2.7% |
| 6.75 | 2.7% | 11.4% |
| 24.0 | 2.9% | 5.0% |
| 24.0 | 2.8% | 3.8% |

Even at the highest volume studied, the addition of NaCl leads to the distribution of iodide amongst the wires being very narrow.

Example 11

Iodination Reaction Using Solid AgI

Wires were prepared as in Example 1, using 500 wires, 51.5 mg NaBr and 2 M NaCl. However, approximately 35 mg of solid AgI was substituted for NaI. When approximately 41 mg of ferricyanide was added (as 1 ml of a 41.2 mg/ml aqueous solution of potassium ferricyanide), AgBr was formed on the wires and the iodide ions from the supernatant suspension of AgI exchanged onto the wires.

Average: 20.2 μg I/wire

Standard Deviation: 0.71

Deviation %: 2.8%

Thus, the iodide tied up as solid AgI was able to exchange to the surface of the silver wires as they were oxidized by the ferricyanide. The variation in the amount of iodide per wire was very low, suggesting that the slow kinetics of release of iodide from the AgI suspension is beneficial to the preparation of the coated wires.

Example 12

One Step Preparation of Silver Iodide Coated Silver Wires: 1500 Wire Batch Size and the Impact of Elevated Concentrations of $NaNO_3$ 1500 wires were prepared as described in Example 1 except that the amount of NaI was increased to 1.0 ml of 0.1 M NaI/0.1 M NaOH, the NaBr was increased to 138 mg, and $K_3Fe(CN)_6$ was increased to 142.2 mg (i.e., 1 ml of a 142.2 mg/ml solution) to account for the increased number of wires. A square 25 ml vial was used to rotate the wires. In addition, the solution was made 3.0 M in $NaNO_3$. The results suggest that this salt is also effective in narrowing the distribution of iodide per wire.

Mean: 12.3 μg I/wire

Standard Deviation: 0.28

Deviation %: 2.3%

Example 13

Preparation of Radioactive Seeds

The method of Example 11 was used to prepare radioactive seeds in a pilot production run. Four runs were carried out with the following results:

| Run # | Target* Activity mCi | Actual* Activity mCi | Computed* Activity mCi | Standard Deviation mCi | % Uptake % |
|---|---|---|---|---|---|
| 1 | 0.34 | 0.34 | 0.31 | 0.01 | 92.78 |
| 2 | 0.41 | 0.45 | 0.41 | 0.02 | 99.02 |
| 3 | 0.34 | 0.38 | 0.34 | 0.01 | 99.18 |
| 4 | 0.40 | 0.45 | 0.40 | 0.01 | 98.91 |

*The target activity is input by the operator while the computed activity is calculated from the actual activity by factoring in the amount of radioactive decay between manufacturing and a time point 2 weeks later. This allows for packaging and shipping at the activity levels required by the physician.

These data demonstrate the utility of the method of the invention, with very good uptake and the achievement of target levels of activity with narrow distributions of activity from wire to wire.

Example 14

Preparation of Radioactive Seeds 2

1334 silver wires, cleaned with heptane and acetone, were loaded into a square 30 ml glass vial together with 13 ml of an aqueous solution of sodium chloride (3.43M) and sodium bromide (0.13M). To this mixture was added 1.08 ml of an aqueous solution of sodium iodide (0.1M) and sodium hydroxide (0.01M) and 1.25 ml of an aqueous solution containing 1.278 Ci sodium [$^{125}$]-iodide. The glass vial was then rotated at an angle of 300 to the horizontal for not less than 1 minute in order to mix the reagents. The rotation was then stopped and 1.27 ml of an aqueous solution prepared from potassium ferricyanide (100 mg/ml) and potassium ferrocyanide trihydrate (12 mg/ml) was added to the reaction vial. Rotation was then restarted and continued for 45 minutes (after which time the solution was clear). The supernatant was removed with a pipette and the wires were washed three times with deionised water. They were then allowed to dry before being loaded into titanium cans, which were subsequently sealed using standard welding techniques.

The completed seeds were assayed and found to have a mean apparent activity of 0.433 mCi with a relative standard deviation of 1.92%.

Example 15

Preparation of High Activity Radioactive Seeds

The method of example 14 was used to prepare radioactive seeds. Four runs were carried out using the following reaction conditions (volumes of reagents were varied according to batch size):

| Run | Number of wires | Vial volume (ml) | Volume NaCl/NaBr (ml) | Volume NaI/NaOH (ml) | Volume ferro/ ferri (ml) | Volume $^{125}$I- iodide (ml) |
|---|---|---|---|---|---|---|
| #245 | 233 | 7.5 | 2.4 | 0.19 | 0.23 | 2.11 |
| #246 | 178 | 7.5 | 2.4 | 0.15 | 0.18 | 2.77 |
| #129 | 226 | 7.5 | 2.4 | 0.17 | 0.22 | 2.48 |
| #130 | 335 | 15 | 3.0 | 0.25 | 0.32 | 3.71 |

The results obtained are shown as follows:

| Run | Mean Activity (mCi) | Standard Deviation (mCi) | % CV |
| --- | --- | --- | --- |
| #245 | 4.025 | 0.0445 | 1.11 |
| #246 | 6.352 | 0.0774 | 1.22 |
| #129 | 5.469 | 0.0550 | 1.01 |
| #130 | 5.589 | 0.0800 | 1.43 |

These data demonstrate the utility of the method of the invention, in particular, the achievement of narrow distribution of seed activity in the high activity range.

It is apparent that many modifications and variations of the invention as hereinabove set forth may be made without departing from the spirit and scope thereof. The specific embodiments described are given by way of example only, and the invention is limited only by the terms of the appended claims.

What is claimed is:

1. A method for the immobilisation of a radioisotope on the metal surface of a substrate of a suitable size and dimensions for incorporation into a source for use in brachytherapy, said method comprising treating the substrate with an oxidizing agent in the presence of a source of a radioactive anion wherein the oxidizing agent is capable of oxidizing the metal to the corresponding metal cation, and the radioactive anion is capable of forming an insoluble salt with said metal cation.

2. The method of claim 1, wherein the metal is selected from the group consisting of silver, gold, copper and lead.

3. The method of claim 2, wherein the metal is silver.

4. The method of claim 1, wherein the radioactive anion comprises $^{125}I$, $^{35}S$ or $^{32}P$.

5. The method of claim 1, wherein the radioactive anion is selected from the group consisting of $^{125}I^-$, $^{131}I^-$, $^{123}I^-$, $^{35}S^{2-}$, $^{35}SO_4^{2-}$, $^{35}SO_3^{2-}$, $^{125}IO_3^-$, $^{131}I_3^-$, $^{123}IO_3^-$, $^{51}CrO_4^{2-}$, $^{32}PO_4^{3-}$, $H^{32}PO_4^{2-}$, $H_2^{32}PO_4^-$ and $H_3^{32}P_2O_7^-$.

6. The method of claim 5, wherein the radioactive anion is $^{125}I^-$.

7. The method of claim 1 which further comprises adding a binding agent.

8. The method of claim 7, wherein the metal is silver and the radioactive anion is $^{125}I^-$.

9. The method of claim 8, wherein the binding agent comprises bromide or chloride ions.

10. The method of claim 1, wherein the oxidizing agent is selected from the group consisting of sodium chlorite ($NaClO_2$), sodium chlorate ($NaClO_3$), sodium chromate ($Na_2CrO_4$), hydrogen peroxide ($H_2O_2$), potassium dichromate ($K_2Cr_2O_7$), potassium permanganate ($KMnO_4$), and potassium ferricyanide ($K_3Fe(CN)_6$).

11. The method of claim 10, wherein the oxidizing agent is potassium ferricyanide.

12. The method of claim 11 which further comprises adding potassium ferrocyanide, to a molar ratio of $Fe(CN)_6^{3-}$-$Fe(CN)_6^{4-}$ of about 10:1 at the start of the oxidising reaction.

13. The method of claim 1, wherein the source of the radioactive anion comprises a solution or dispersion.

14. The method of claim 1, wherein the immobilisation takes place in a solution comprising an elevated concentration of a salt additive.

15. The method of claim 14, wherein the salt additive is NaCl, KCl, CsCl, LiCl, $CaCl_2$, $NaNO_3$ or $MgCl_2$.

16. The method of claim 14, wherein the concentration of the salt additive is in the range of about 0.01 molar to the saturation level of the added salt.

17. The method of claim 1 wherein the source of the radioactive anion comprises two or more radioisotopes.

* * * * *